United States Patent [19]

Reno et al.

[11] Patent Number: 5,217,705
[45] Date of Patent: Jun. 8, 1993

[54] METHOD OF DIAGNOSING BLOOD CLOTS USING FIBRIN-BINDING PROTEINS

[75] Inventors: John M. Reno, Brier; Stephen W. Hadley, Seattle, both of Wash.; Marjorie A. Mohler, Burlingame, Calif.

[73] Assignee: Neorx Corporation, Seattle, Wash.

[21] Appl. No.: 247,973

[22] Filed: Sep. 22, 1988

Related U.S. Application Data

[63] Continuation-in-part of Ser. No. 101,329, Sep. 25, 1987, abandoned.

[51] Int. Cl.$^5$ .................... A61K 49/02; A61K 43/00
[52] U.S. Cl. .................... 424/1.1; 530/402; 530/409; 530/410; 530/380; 930/280; 424/9
[58] Field of Search ............ 424/1.1; 530/380, 402, 530/409, 410; 930/280

[56] References Cited

U.S. PATENT DOCUMENTS

| | | | |
|---|---|---|---|
| 4,318,904 | 3/1982 | Shaw et al. | 514/18 |
| 4,381,346 | 4/1983 | Huasin et al. | 424/1.1 X |
| 4,416,865 | 11/1983 | Rhodes et al. | 424/1.1 |
| 4,418,052 | 11/1983 | Wong | 424/1.1 |
| 4,425,319 | 1/1984 | Yokoyama et al. | 424/1.1 |
| 4,427,646 | 1/1984 | Olexa et al. | 424/1.1 |
| 4,663,146 | 5/1987 | Morser et al. | 424/1.1 |
| 4,741,900 | 5/1988 | Alvarez et al. | 424/1.1 |
| 4,741,903 | 5/1988 | Smith | 514/2 X |
| 4,913,891 | 4/1990 | Fowler et al. | 424/1.1 |

FOREIGN PATENT DOCUMENTS

| | | |
|---|---|---|
| 237332 | 9/1987 | European Pat. Off. . |
| 247866 | 12/1987 | European Pat. Off. . |
| PCTWO84/0-1960 | 5/1984 | PCT Int'l Appl. . |
| WO88/03559 | 5/1988 | PCT Int'l Appl. . |

OTHER PUBLICATIONS

Baker et al., *European Journal of Nuclear Medicine* (1985) 10:155-159.
Kettner and Shaw, *Thrombosis Research* 14; 969-973.
Kettner and Shaw, *Methods in Enzymology*, vol. 80, [63] 826-842.
Kettner and Shaw, *Biochemistry*, vol. 17, No. 22, 1978.
Collen et al., Leuven, Belgium, and Upton, N.Y., "In Vivo Studies of a Synthetic Inhibitor of Thrombin", *J. Lab. Clin. Med.*, Jan. 1982.
Hnatowich et al., *Eur. J. Nucl. Med.* (1987) 13:467-473, "Characterization of indium-111 labeled recombinant tissue plasminogen activator for the imaging of thrombi".
International Search Report in the International (PCT) patent application that corresponds to U.S. Ser. No. 07/247.973.

*Primary Examiner*—Robert L. Stoll
*Assistant Examiner*—John M. Covert

[57] ABSTRACT

A fibrin-binding protein such as t-PA is labeled with a detectable substance, such as a radionuclide, and administered to a patient for diagnosis of blood clots and for monitoring the dissolution thereof during therapy. The detectable substance preferably is attached to t-PA through linkers which specifically bind to the portion of the t-PA protein responsible for enzymatic activity, thereby diminishing this activity while leaving the fibrin-binding property of the protein intact.

11 Claims, 6 Drawing Sheets

IMMEDIATE

5 MIN.

10 MIN.

15 MIN.

SYNTHESIS OF Phe-Pro-Arg-CH$_2$Cl (PPACK)

Direct Coupling of PPACK to $N_2S_2$ Ligand NHS ester

METHOD OF DIAGNOSING BLOOD CLOTS USING FIBRIN-BINDING PROTEINS

CROSS-REFERENCE TO RELATED APPLICATIONS

This application is a continuation-in-part of application Ser. No. 101,329, filed on Sep. 25, 1987 now abandoned.

TECHNICAL FIELD

The present invention relates to methods for detecting fibrin deposits within the body. Fibrin-binding proteins having detectable substances, e.g., radionuclides, attached thereto are provided for diagnosing fibrin deposits, such as blood clots, and for monitoring the dissolution thereof during therapy.

BACKGROUND ART

Fibrin is an insoluble protein which is produced at the site of a wound through a chain reaction involving formation and activation of certain vascular proteins. A fibrous network of fibrin forms at the wound site and combines with blood platelets, thus producing a fibrin-platelet clot which stops the flow of blood from the wound. Fibrin-platelet clot formation is thus essential for the survival of humans and other animals. However, fibrin-platelet clot formation elsewhere in the body (i.e., at locations other than wound sites) causes a dangerous, potentially life-threatening restriction of blood flow. Blood clots, also known as thrombi, may remain at the original point of formation or may dislodge and travel through the bloodstream to a new site where the clot causes a sudden blocking of blood flow. Examples of the medical problems caused by abnormal fibrin-platelet clots include venous and arterial thromboses, heart attacks caused by thrombi in heart vessels, as well as pulmonary and cerebral thromboembolism. In addition, fibrin-platelet clots have been reported to occur at sites of infarcts and tumors, wherein fibrin may surround the damaged tissue or tumor, thus further aggravating the patient's condition. (See U.S. Pat. No. 4,418,052.) In view of the high incidence of medical problems associated with abnormal fibrin-platelet clots, much effort has been directed to development of techniques for diagnosing such conditions. Unfortunately, many of these techniques suffer from lack of specificity or reliability, while others require unacceptable lengths of time to complete the testing. Still other methods are designed to detect thrombi in the process of forming, but not preexisting clots.

Among the diagnostic methods which have been attempted is the use of radiolabeled proteins, such as enzymes, which either bind to or become incorporated within a clot, so that the clot can be imaged using techniques for detection of the radioisotope within the body. Such proteins include streptokinase, urokinase, tissue plasminogen activator, fibrokinase, streptokinase-activated human Plasmin, fibrin and certain fragments thereof. (See, for example, U.S Pat. Nos. 4,427,646; 4,416,865; 4,418,052; and 4,663,146.) However, such problems as low specificity or affinity of the radiolabeled protein for a clot, denaturation of the protein during the radiolabeling procedures, and unstable attachment of the radioisotope to the protein have been associated with certain of these proposed diagnostic techniques. Thus, a need remains for an accurate, convenient method for early detection of abnormal fibrin-platelet clots within the body.

SUMMARY OF THE INVENTION

The present invention provides a method for detecting a fibrin deposit in vivo, comprising the steps of:

(a) administering to a patient suspected of having a fibrin-platelet clot a labeled thrombolytic protein, wherein the thrombolytic protein's clot-dissolving activity is reduced or eliminated and the label is selectively attached to a portion of the thrombolytic protein other than the fibrin-binding domain; and (b) detecting the pattern of biodistribution of the labeled thrombolytic protein in the patient.

Thrombolytic proteins include such proteins as plasmin and plasminogen activators such as streptokinase, streptodornase and urokinase. Preferably, the administered thrombolytic protein is tissue-type plasminogen activator (t-PA) having reduced plasminogen-activating activity, wherein the detectable substance attached thereto is a radioisotope such as $^{99m}$Tc in the form of a chelate.

In one embodiment of the invention, the detectable substance is attached to the thrombolytic protein through a linker which may bind to a portion of the thrombolytic protein responsible for the clot-dissolving activity or at such other portion of the thrombolytic protein to reduce or eliminate the thrombolytic activity. Reducing the activity prolongs localization of the protein at the fibrin deposit in vivo and helps minimize side effects associated with administration of protein having clot-dissolving activity.

The present invention also provides a method for making a labeled thrombolytic protein, comprising attaching a detectable substance to the thrombolytic protein through a linker wherein the attachment of the linker is to a portion of the thrombolytic protein other than the fibrin-binding domain.

Also provided by the present invention are fibrin-binding proteins having detectable substances attached thereto, wherein the detectable substance is specifically attached to a portion of the protein other than the fibrin-binding domain. Specifically, t-PA having a radioisotope attached thereto through a linker which binds specifically to the portion of the t-PA protein responsible for plasminogen activation is provided. This t-PA protein of the invention has reduced or substantially eliminated plasminogen-activating activity (depending on how much of the linker is bound thereto), and an intact fibrin-binding domain.

The proteins of the present invention are administered for in vivo diagnosis of fibrin deposits such as blood clots and for monitoring the dissolution thereof during therapy. Kits useful for preparation of radiolabeled, fibrin-binding proteins of the invention also are disclosed herein.

DETAILED DESCRIPTION OF THE INVENTION

Figure 1:
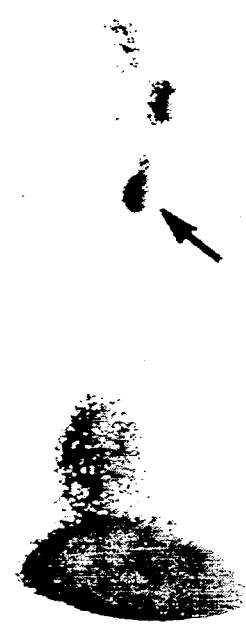
FIG. 1 shows gamma camera images of rabbits taken at the time points indicated, following injection of radiolabeled t-PA to image blood clots in the animals.
Figure 1:
Figure 1:
Figure 1:

The present invention provides a method for diagnosing fibrin-platelet clots within the body and for monitoring the dissolution of such clots during therapeutic treatment. The method comprises administration of a labeled thrombolytic protein, wherein any clot-dissolving activity of the thrombolytic protein has been reduced or substantially eliminated prior to administration. The fibrin binding property of the protein is preserved by selectively attaching the detectable substance to a portion of the protein other than the fibrin-binding domain. Procedures for detection of the distribution of the detectable substance within the body are employed to locate any fibrin-platelet clots, such as fibrin-platelet clots associated with myocardial infarcts or tumors. Reduction or elimination of the clot-dissolving activity serves to allow completion of the detection step before the bound protein is released from the fibrin-platelet clot through the process of clot dissolution. In addition, use of a thrombolytic protein having reduced or eliminated clot-dissolving activity as a diagnostic agent allows a physician to avoid unnecessarily inducing side effects associated with administration of clot-dissolving enzymes in a patient who may not be afflicted with fibrin-platelet clots. Following diagnosis of a clot, periodic administration of the labeled thrombolytic protein of the present invention during therapy may be used to monitor various therapeutic treatments in order to ensure complete dissolution of the clot. While the widest use of this invention is in human medical therapy the invention is equally applicable in a veterinary setting.

The invention also provides a method for attaching a detectable substance specifically to a non-fibrin-binding portion of the thrombolytic protein, such that the fibrin-binding property of the thrombolytic protein is not diminished by labeling with the detectable substance. Reduction of the fibrin-binding property of a labeled thrombolytic protein may decrease its effectiveness as a clot-imaging agent, since the clot residence time would be shortened. In addition, higher "background" on images might result from the increased portion of the administered labeled protein which would not be localized at the clot site. A detectable substance may be selectively attached outside the fibrin-binding domain of a protein using linkers that are described below.

The thrombolytic protein which is administered in accordance with the present invention is any thrombolytic protein which binds to fibrin in vivo. The thrombolytic protein may be naturally occurring or may have been engineered to contain a fibrin-binding domain, e.g., through genetic engineering techniques. Advantageously, the thrombolytic protein is naturally occurring in the patient to which it is to be administered, to reduce the chances of an adverse immunological response. Known naturally-occurring fibrin-binding proteins include, but are not limited to, the plasminogen activators such as urokinase (UKS) and tissue-type plasminogen activator (t-PA). Plasminogen activators are enzymes which catalyze the conversion of the inactive precursor plasminogen to plasmin, which also binds fibrin and has fibrin-dissolving activity. Tissue plasminogen activator is a serine protease recognized as having a much higher affinity for fibrin than does urokinase, wherein the enzymatic activity of t-PA is localized at fibrin deposit sites, so t-PA is generally preferred for use in the present invention. Methods of isolating t-PA from certain cell lines (e.g., Bowes melanoma cells) have been described, and methods for producing t-PA through recombinant DNA technology also are known (see British patent application GB 2,119,804).

The protein is treated to reduce the clot-dissolving activity thereof while maintaining its fibrin-binding property. The term "clot-dissolving activity," as used herein, refers to any biological activity of the protein which causes, directly or indirectly, breakdown of fibrin and, therefore, dissolution of a fibrin-platelet clot. The t-PA enzyme does not directly dissolve clots, but catalyzes the formation of the clot-dissolving protein plasmin from plasminogen. Therefore, for t-PA, the plasminogen. activating biological activity is considered to be the "clot-dissolving activity," as used herein.

The clot-dissolving (i.e., fibrin-degrading) activity of the protein is reduced to a degree sufficient to allow completion of the detection step before the thrombolytic protein is released from the clot site. In addition to prolonging localization of the thrombolytic protein at the fibrin deposit site, reduction of the clot-dissolving activity also serves to minimize side effects associated with administration of proteins having such activity. It has been discovered that reduction of the clot-dissolving activity is advantageous in order to detect accurately the location of a fibrin-platelet clot within the body. As described in more detail below, when a clot-dissolving protein (having its native, undiminished clot-dissolving activity) binds to a clot in vivo, localized degradation of the fibrin begins, which results in release of the thrombolytic protein from the original fibrin-platelet clot site, especially when the protein is bound primarily to the outer surface of the clot. Therefore, the biodistribution of the protein, and the detectable substance attached thereto, will become progressively more diffuse. There will only be a short period of time in which a sufficient amount of the detectable substance has accumulated at a fibrin-platelet clot to give a strong localized signal or image before dispersion begins. Therefore, the physician may conclude that there never was a fibrin-platelet clot, and may subject the patient unnecessarily to further testing. Reduction or elimination of the enzymatic activity of t-PA, when used in the method of the present invention, is especially important, because the activity of t-PA is known to increase dramatically in the presence of fibrin.

The clot-dissolving activity of the thrombolytic protein may be reduced by any suitable means as long as the fibrin-binding property is maintained. In the case of production through recombinant DNA technology, the cloned gene which encodes the protein may be altered to diminish the clot-dissolving activity, e.g., through known methods of creating insertions, deletions and other mutations in the gene. For example, the isolated gene may be subjected to restriction enzyme digestion, alone or in combination with other enzymatic treatments, such as digestion with certain nucleases, to excise a portion or all of the gene segment which encodes the portion of the protein responsible for the clot-dissolving activity. Other known procedures, such as site-directed mutagenesis, may be used to inactivate the clot-dissolving activity (See Old and Primrose, *Principles of Gene Manipulation.* 2nd Ed., University of California Press, Los Angeles, page 164.) Alternatively, the protein itself may be fragmented and the fibrin-binding portion thereof purified by known techniques, such as affinity chromatography. Chemical treatment of the protein to decrease the clot-dissolving activity thereof, while maintaining the fibrin-binding property, is yet another option. One embodiment of the present invention, described in more detail below, involves reacting the protein with a chemical compound which selectively binds to the portion of the protein responsible for the fibrin-platelet clot-dissolving activity, wherein binding of the chemical compound to this portion of the protein reduces said activity. The chemical compound may bind to the protein reversibly or irreversibly, or may be a suicide inhibitor. When the protein is to be administered in vivo, an irreversible inhibitor (that is covalently bound to the protein) preferably is used.

The detectable substance attached to the thrombolytic protein may be any substance which may be stably attached to the protein without significantly reducing the fibrin-binding property thereof, safely administered to a patient, and detected by a suitable known technique. The detectable substance may be attached to the protein directly or through various linker or adaptor molecules, including certain affinity ligands, as discussed below. Among the suitable detectable substances are nuclear magnetic resonance contrast agents, X-ray contrast agents, and radioisotopes, including, but not limited to, radioisotopes of iodine (e.g., $^{131}I$ or $^{123}I$) indium (e.g. $^{111}In$), bromine (e.g., $^{75}Br$ or $^{76}Br$), or fluorine (e.g. $^{18}F$). These diagnostic agents are detectable by external (non-invasive) means. A preferred radioisotope for use in the present invention is the radionuclide $^{99m}$technetium ($^{99m}Tc$). The six-hour half-life of $^{99m}Tc$, as well as its compatibility with gamma camera scanning devices and its availability in most hospitals and clinics, makes it a favored radionuclide for use in diagnostic procedures.

Methods for radiolabeling proteins with various radioisotopes are well known. These procedures include attachment of the radioisotope directly to the protein, or attachment through various chelators and other linking compounds which react with various functional groups on the protein to bind the radioisotope thereto. See, for example, U.S. Pat. Nos. 4,652,440; 4,659,839; and 4 472 509. and British patent application GB 2,109,407. However, non-specific attachment of radiolabeled compounds to fibrin-binding proteins may result in a decrease in the ability of the protein to bind to fibrin, since a portion of the radioisotopes will be attached to the fibrin-binding domain. In accordance with the present invention, the detectable substance (e.g. radioisotope) preferably is selectively attached outside of the fibrin-binding domain of the protein.

The labeled thrombolytic proteins of the present invention are useful as diagnostic agents and for monitoring dissolution of a fibrin-platelet clot during therapy. As would be known to the ordinarily skilled artisan, the amount injected into a particular patient will depend on such factors as the affinity of the particular protein for fibrin, the nature of the detectable substance attached thereto, and, when the substance is a radioisotope, the specific activity of the preparation. The amount injected is sufficient for detection of the pattern of biodistribution of the substance in vivo by appropriate detection devices after administration to the patient.

The labeled thrombolytic protein may be injected in any suitable physiologically acceptable carrier. Suitable carriers will not denature or otherwise alter the protein, or cause the protein to precipitate from solution, and are nontoxic in the patient. Suitable carriers include, but are not limited to, aqueous solutions, preferably isotonic, comprising sodium chloride or other salts, glucose, dextrose, or water for injections.

After injection of a labeled thrombolytic protein of the invention into the patient, the detection procedure is delayed for a sufficient length of time to a allow binding of the labeled thrombolytic protein at the site of any fibrin-platelet clots which may be present. The appropriate length of time will depend on such factors as the degree of specificity or affinity of the thrombolytic protein for fibrin, the nature of the detectable substance (e.g., the half-life of a particular radio-isotope), the efficiency with which injected labeled thrombolytic protein which does not become bound to a fibrin-platelet clot is cleared from the body, the site of injection and the resulting route the protein must travel to the clot site, etc. In general, sufficient time is allowed to pass to allow substantial clearance of the non-bound portion of the protein from the bloodstream. Certain of the thrombolytic proteins of the invention will be cleared from the patient through a particular organ (e.g., the liver), and the route of clearance from the body may vary according to the nature of the thrombolytic protein. Such organs will not be interpreted as fibrin deposit sites when the pattern of biodistribution is detected.

Once the presence of a fibrin-platelet clot has been diagnosed, therapy with any suitable agents, or mixtures thereof, is begun. Known therapeutic reagents include the enzymes streptokinase, urokinase and t-PA, and anticoagulants, such as heparin. These agents are administered in accordance with conventional procedures, in non-labeled form. Many of the current methods for monitoring dissolution of blood clots during treatment suffer from a lack of ability to distinguish between partial and complete restoration of blood flow. The proteins of the present invention can be administered in conjunction with administration of therapeutic agents to determine when the clot has been effectively dissolved (i .e., when fibrin deposits are no longer detected in accordance with the method of the invention) and treatment then can be ended. Monitoring of treatment procedures in this manner reduces the incidence of premature termination of treatment, which has been a problem in the past.

The present invention also provides a method for labeling a thrombolytic protein while preserving the activity of the fibrin binding of the thrombolytic protein, comprising attaching a detectable substance to the thrombolytic protein through a linker, wherein the attachment of the linker is to a portion of the thrombolytic protein other than the fibrin binding domain. This method is especially advantageous for thrombolytic proteins containing a clot dissolving domain that is inactivated (or susceptible to a reduction in the biological activity thereof) by attachment of detectable substances to that clot dissolving domain.

Included in the invention are thrombolytic proteins having an attached detectable substance, wherein the substance is attached to the clot dissolving domain which reduces or eliminates the clot dissolving activity while not affecting another activity, e.g. fibrin binding. The protein may be a thrombolytic enzyme that comprises both an enzymatic activity and a fibrin binding domain, wherein preservation of the biological activity of the fibrin binding domain is desired. A linker that binds specifically to the portion of the enzyme that is responsible for enzymatic activity is used. The activity of other functional domains (e.g., a substrate-binding domain) thus is preserved after attachment of the detectable substance to the thrombolytic protein through the linker.

A number of compounds that bind to the portion of an enzyme that confers the enzymatic activity are known, and may be used, or modified for use, as linkers in accordance with the present invention. Such compounds include but are not limited to, affinity labeling reagents. These reagents are used for such purposes as identification and characterization of enzymes, as well as the inactivation of certain enzymes in in vitro assays. One group of affinity labeling reagents includes oligopeptide chloromethyl ketone compounds, which generally comprise from two to about four amino acid residues and often are derived from a particular enzyme's substrate. These compounds bind covalently (irreversibly) to an enzyme's active site, thereby inactivating the enzyme. Oligopeptide chloromethyl ketone compounds that inactivate certain enzymes (e.g. serine proteases, especially trypsin-like serine proteases) are known. Oligopeptide chloromethyl ketone inactivators of kallikreins, plasmin, thrombin, urokinase, and other proteases are described by Kettner and Shaw in *Methods in Enzymology*. Vol. 80, pp 826–842 (1981) and *Biochemistry*. Vol. 17, pp. 4778–4784 (1978). These inhibitors, and the use thereof as linkers, are further described below.

In one embodiment of the invention, a detectable substance is attached specifically to a thrombolytic protein having a fibrin-binding domain, without diminishing the fibrin-binding property of the protein, by attaching the detectable substance to the protein through a linker which binds specifically to a portion of the thrombolytic protein other than the fibrin-binding domain. The fibrin-binding domain is the portion of the protein which imparts to the protein the ability to bind to fibrin. The linker may be any suitable compound which binds the detectable substance, on the one hand, and attaches to the protein at a site distant from the fibrin-binding domain. Suitable linkers include, but are not limited to, various affinity ligands which bind specifically with portions of the protein other than the fibrin-binding portion. For example, the detectable substance may be attached to the portion of the protein responsible for clot-dissolving activity, wherein this attachment causes a reduction in said activity, while the portion of the protein responsible for fibrin binding remains unaffected.

One method of accomplishing this specific attachment involves binding the detectable substance to the protein through oligopeptide derivative linker molecules, wherein the linkers attach specifically to the portion of the protein responsible for clot-dissolving activity, thereby diminishing said activity. Likewise, the reduction in fibrin binding which may result from nonspecific attachment of a detectable substance to all portions of a protein (including the portion responsible for fibrin binding), is minimized by this approach. Examples of such oligopeptide derivative linkers are those believed to inactivate a particular enzyme by mimicking the portion of the particular polypeptide substrate with which the enzyme interacts naturally. Examples of such linkers are "chloromethyl ketone" tripeptide suicide enzyme inhibitors. The chloromethyl ketone moiety of the inhibitor molecule inactivates the enzyme by alkylating the histidine residue within the enzyme's active site. One of several such inhibitors is the tripeptide derivative glutamic acid-glycine-arginine-chloromethyl ketone, which is commercially available from Calbiochem Biochemicals, San Diego, as a urokinase inhibitor. Another is D-phenylalanine-L-proline-L-arginine-chloromethyl ketone, which is abbreviated as "D-Phe-Pro-Arg-CH$_2$Cl" hereinafter and is sold as "PPACK" by Calbiochem as a thrombin inhibitor. This thrombin inhibitor was described by Kettner and Shaw (*Thrombosis Research* 14: 969–973). It has been found that D-Phe-Pro-Arg-CH$_2$Cl also inhibits t-PA. (Mohler, M. et al., Thromb. and Haem. 52 (2):160–164 [1986].) Another tripeptide derivative that binds to the portion of t-PA responsible for enzymatic activity is Tyr-Pro-Arg-CH$_2$-Cl.

In accordance with one embodiment of the present invention, the compound D-Phe-Pro-Arg-CH$_2$Cl or Tyr-Pro-Arg-CH$_2$Cl is used as a linker for specific binding of a radiolabeled molecule (e g., a chelate comprising a radionuclide metal) to the portion of the t-PA protein responsible for catalyzing the conversion of plasminogen to plasmin. It has been found that attachment of a radionuclide chelate to t-PA through this tripeptide linker results in both stable covalent attachment of the radionuclide to the protein and reduction of the plasminogen-activating activity of the enzyme, while the fibrin-binding property is retained. Thus, one set of chemical reactions accomplishes two goals, namely, specific radiolabeling of the protein and simultaneously reducing the enzymatic activity.

The present invention provides compounds of the following formula:

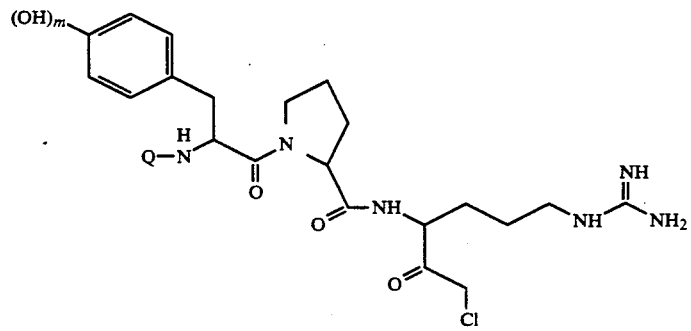

wherein m is 0 or 1 and Q represents a radiolabeled molecule. When m is 0, the tripeptide chloromethyl ketone linker is D-Phe-L-Pro-L-Arg-CH$_2$Cl. When m is 1, the linker is Tyr-L-Pro-L-Arg-CH$_2$Cl. Among the many radiolabeled molecules that these compounds may comprise are the radionuclide metal chelates and radiohalogenated molecules described below. Also provided by the present invention is the protein t-PA having a radiolabeled molecule attached thereto through one of the above-described tripeptide-CH$_2$Cl linkers that binds to t-PA.

Many chelating compounds of various structures are known. The chelating compound which is attached to the PPACK or Tyr-Pro-Arg-CH$_2$Cl linker may be any compound capable of reacting with the amino terminus of the linker to form a bond thereto and which comprises donor atoms capable of forming bonds with a radionuclide to form a stable chelate of the radionuclide. The chelating compound may be bonded to the tripeptide linker through a bifunctional adaptor molecule comprising one functional group reactive with the free amino group on the phenylalanine or tyrosine residue of the linker molecule and a second functional group reactive with a group on the chelating compound. Many such adaptors are known, with the necessity for an adaptor and the choice thereof being dependent on the chemical structure of the chelating compound.

One of the many chelating compounds which may be bound to the D-Phe-Pro-Arg-CH$_2$Cl or other tripeptide linker is a chelating compound having the following formula:

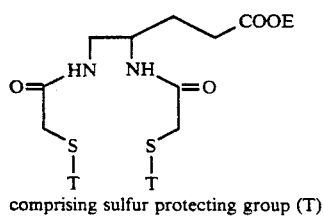

comprising sulfur protecting group (T)

wherein "E" represents an active ester group. This "N$_2$S$_2$" chelating compound, which has been described in European patent application publication no. 188,256, (hereby incorporated by reference) comprises an active ester group which will react with the free amine of the tripeptide linker to form an amide bond. The tripeptide linker may be synthesized and the N$_2$S$_2$ chelating compound attached to the D-Phe-Pro dipeptide before the Arg-CH$_2$Cl portion of the linker is attached, as described in Example 2 below. It has been found that when the chelating compound is reacted with the intact tripeptide, a certain percentage of the chelating compound reacts with a free amino group on the arginine residue (which interferes with interaction of the resulting tripeptide derivative with t-PA) rather than reacting with the terminal NH$_2$ group on the phenylalanine residue. However, the pH of the reaction mixture may be adjusted (e.g., to about 5 to 7) to promote selective reaction of the ester on the chelating compound with the amine on the phenylalanine (rather than the arginine) residue. The chelating compound thus may be reacted with the intact tripeptide.

The chelating compound may be reacted with a metal radionuclide, such $^{99m}$Tc, as described in the European application no. 188,256 and in the examples below, to form the corresponding chelate in which the radionuclide metal is held by four separate covalent bonds to the two nitrogen and two sulfur donor atoms. The tripeptide linker having the chelate attached thereto is then reacted with t-PA, wherein the linker becomes attached to the portion of the t-PA enzyme responsible for activation of plasminogen, as described above. The resulting radiolabeled t-PA protein is administered to diagnose fibrin deposits or to monitor the progress of a therapeutic treatment.

A number of other radiolabeled molecules may be attached to a fibrin-binding protein through a linker that binds outside the fibrin-binding domain. Chelating compounds comprising various combinations of sulfur, nitrogen, oxygen, and phosphorous donor atoms may be used. Many such chelating compounds, as well as methods for the synthesis and radiolabeling thereof to produce metal radionuclide chelates, are known. In one embodiment of the invention, the chelating compound comprises a total of four donor atoms selected from nitrogen and sulfur atoms. During the radiolabeling procedure, bonds form between the donor atoms and the radionuclide metal. In addition to the N$_2$S$_2$ chelating compound described above, compounds comprising three nitrogen and one sulfur donor atoms may be used. Examples of such "N$_3$S" compounds include those of the following formula:

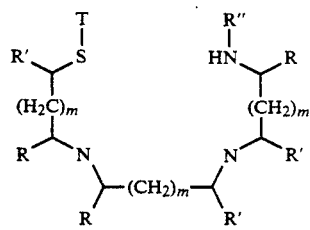

wherein:

T is a sulfur protecting group, such as a group that, together with the sulfur donor atom to which it is attached, defines a thioacetal or hemithioacetal group;

each R independently represents H$_2$ or =O;

each R' independently represents a substituent selected from the group consisting of hydrogen, a non-alkyl side chain of an amino acid other than cysteine, alkyl, geminal dialkyl, and, (CH$_2$)$_n$—Z;

Z represents —COOH or a functional group that will react with a linker to join the chelating compound to the linker;

m represents 0 or 1, with the proviso that at most one m represents 1;

n is an integer of from 1 to about 4; and

R" is hydrogen; —(CH$_2$)n—Z; or an alkyl group having one or more polar groups substituted thereon;

wherein the compound comprises at least one —(CH$_2$)n—Z substituent.

Radiolabeling of this N$_3$S chelating compound in accordance with the invention produces a radionuclide metal chelate of the following formula:

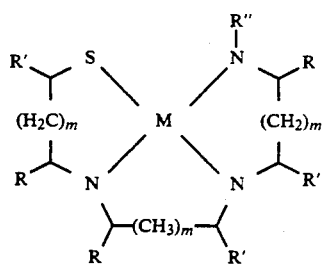

wherein M represents a radionuclide metal or oxide thereof and the other symbols are as described above.

Methods for synthesizing various $N_3S$ chelating compounds are known. See, for example, European patent application publication number 173,424.

Other chelating compounds may have different combinations of donor atoms. Such compounds include $N_2S_4$, $N_2S_3$, and $N_3S_3$ chelating compounds, among others. In addition, the $N_2S_2$ and $N_3S$ compounds presented above may comprise varying numbers of substituents such as carboxylic acid groups and from 0 to 3 oxygen atoms (=O) attached to carbon atoms of the chelate core.

Other examples of radiolabeled molecules that may be attached to fibrin binding proteins in accordance with the present invention include radiohalogenated molecules.

Radiohalogens useful for diagnostic imaging include, but are not limited to, $^{123}I$ for imaging by scanning the patient with a gamma camera, and $^{18}F$, $^{75}Br$, or $^{76}Br$ for positron tomographic imaging.

Examples of molecules that bind radiohalogens at the meta or para position on a phenyl ring are described in European patent application publication number 203,764, which is hereby incorporated by reference. These compounds may be represented by the following formula:

*X—Ar—R wherein
  *X is a radioisotope of iodine, bromine, fluorine, or astatine;
  Ar is an aromatic or heteroaromatic ring;
  R is a chemical bond or a substituent containing 1 to 12 straight-chain carbon atoms that does not activate Ar toward electrophilic substitution on the order produced by hydroxy or amino substitution of the ring. The bond or substituent has attached thereto a conjugation group, which is a functional group suitable for reaction with a linker to bind the radiohalogenated molecule thereto. *I-para-iodophenyl compounds (in which *I represents a radioisotope of iodine) may be prepared using the procedures described in EP 203,764, which generally involve substituting the organometallic group $Sn(n-Bu)_3$ or $SnMe_3$ on a haloaromatic compound. A radioisotope of a halogen then is substituted for the organometallic group by halodemetalization. Examples of radiohalogenated molecules that may be prepared using such a procedure are represented by the following formulas:

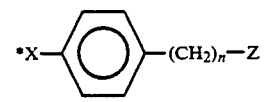

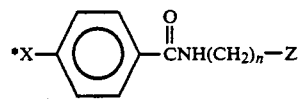

wherein n represents an integer from 0 to 3, Z represents a conjugation group, and *X represents a radioisotope of a halogen.

In one embodiment of the invention, the conjugation group is a group that will react with a linker that binds outside the fibrin binding domain of a fibrin binding protein, e.g., a tripeptide-chloromethyl ketone linker that binds to (and inhibits) t-PA. The conjugation group may be an active ester that reacts with a primary amine on the linker to form an amide bond. Among the many suitable esters are 2,3,5,6-tetrafluorophenyl ester, thiophenyl ester, and N-hydroxysuccinimidyl ester. The above, described radiohalogenated molecules thus may be attached to t-PA outside the fibrin-binding domain through the above-described tripeptide derivative linkers.

Alternatively, the fibrin-binding protein may be radioiodinated using a Bolton-Hunter reagent i.e., N-succinimidyl-3-(4-hydroxyphenyl)propionate or water-soluble derivatives thereof. Methods for radioiodinating these reagents (wherein the radioisotope is substituted ortho to the hydroxyl on the aromatic ring) are known. See, for example, Bolton and Hunter (*Biochem. J.* 33 529–539 [1973]) as well as page 295 of the Pierce Chemical Company 1988 Handbook and General Catalog. The resulting radioiodinated molecules are represented by the following formulas:

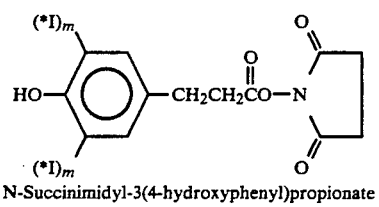

N-Succinimidyl-3(4-hydroxyphenyl)propionate

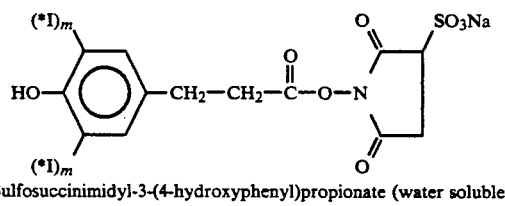

Sulfosuccinimidyl-3-(4-hydroxyphenyl)propionate (water soluble)

wherein *I represents a radioisotope of iodine and m is 0 or 1 (with at least one m being 1). Additional methylene groups may be inserted between the aromatic ring and the ester group.

In accordance with one embodiment of the present invention, the succinimidyl ester group of the radioiodinated Bolton-Hunter reagent is reacted with a free amine group on a linker that binds outside the fibrin-binding domain of a fibrin-binding protein. The radioiodinated reagent may be joined to t-PA through one of the above-described tripeptide chloromethyl ketone linkers, for example.

In another embodiment of the present invention, a radiohalogen may be attached directly to a tripeptide linker. The radiohalogen may be substituted onto the aromatic ring of a phenylalanine or tyrosine residue in a tripeptide linker. Procedures for producing such radiohalogenated linkers include those presented in Examples 4 and 5 below.

The degree to which the clot-dissolving activity of a particular protein is reduced is related to the amount of specific linker compound (e.g., tripeptide linker) attached thereto. If further reduction of enzymatic activity is desired, additional labeled (e.g., radioisotope-labeled) or unlabeled linker compound may be reacted with the protein.

In some cases, it may be desirable to avoid completely destroying all plasminogen-activating activity of the t-PA protein. A low level of residual enzymatic activity may serve to "open up" a clot sufficiently to allow binding of the radiolabeled t-PA within the clot, as opposed to only the outer surface of the clot. Improved images may result.

In one embodiment of the invention, a kit is provided for use in preparing the radiolabeled, fibrin-binding protein of the invention. An example of such a kit is one comprising a first vial containing t-PA. A second vial contains a lyophilized preparation comprising three reagents:

(a) $N_2S_2$-D-Phe-Pro-Arg-CH$_2$Cl (a molecule comprising an $N_2S_2$ chelating compound attached to the previously described D-Phe-Pro-Arg-CH$_2$Cl linker, which is synthesized as described in Example 2 below).

(b) A reducing agent effective in reducing pertechnetate ($^{99m}$TcO$_4$-which is in the +7 oxidation level) to a lower oxidation state at a neutral to acidic pH so that a technetium exchange complex can be formed. Many suitable reducing agents are known, including, but not limited to, stannous ion (e.g., in the form of stannous salts, such as stannous chloride or stannous fluoride), metallic tin, formamidine sulfinic acid, ferrous chloride, ferrous sulfate, ferrous ascorbate, and alkali salts of borohydride. Preferred reducing agents are stannous salts.

(c) An exchange agent with which the reduced $^{99m}$Tc will form an exchange complex, thus protecting the $^{99m}$Tc from hydrolysis. In order to achieve efficient transfer or exchange of the $^{99m}$Tc from this complex to the chelating compound, the exchange agent advantageously binds the radionuclide more weakly than the chelating agent will. Exchange agents which may be used include, but are not limited to, gluconic acid, glucoheptonic acid, methylene diphosphonate, glyceric acid, glycolic acid, mannitol, oxalic acid, malonic acid, succinic acid, bicine, N,N-bis(2-hydroxyethyl) ethylene diamine, citric acid, ascorbic acid, and gentisic acid. Good results are obtained using gluconic acid or glucoheptonic acid as the exchange agent.

Pertechnetate is combined, in aqueous solution, with the contents of the second vial. The pertechnetate is reduced and bound by the exchange agent, then transferred to the $N_2S_2$ chelating compound to form a stable chelate. The resulting $^{99m}$TcN$_2$S$_2$-D-Phe-Pro-Arg-CH$_2$Cl is reacted with the t-PA under physiologically acceptable conditions (i.e., reaction conditions which will not denature the t-PA) to form the radiolabeled t-PA of the present invention.

A stannous chloride reducing agent may be combined with a gluconic acid exchange agent to form a stannous gluconate complex, which therefore functions as ingredients (b) and (c). $^{99m}$Tc-radiolabeled t-PA is prepared, using such a kit, generally as described in Example 2 below.

The kit optionally may comprise additional vials containing various buffers, additional reagents used during the radiolabeling procedures, stabilizers, or other such compounds. The procedures for preparation of a radiolabeled protein using the kits are conducted under sterile conditions.

The following examples are provided to illustrate certain embodiments of the present invention and are not intended to limit the scope of the claims which follow.

EXAMPLE I

Preparation of $^{99m}$Tc $N_2S_2$ chelate-t-PA conjugates, with and without a D-Phe-Pro-Arg-CH$_2$Cl linker A vial of freeze-dried t-PA was reconstituted with sterile water to about 5 mg/ml. The buffer was exchanged by gel filtration into 0.25M NaPi (sodium phospate) 0.3M guanidine, pH 7.5. Guanidine was added to keep the t-PA in solution. Labeling was done with a preformed $N_2S_2$ chelate comprising a 2,3,5,6-tetrafluorophenyl active ester having the following formula:

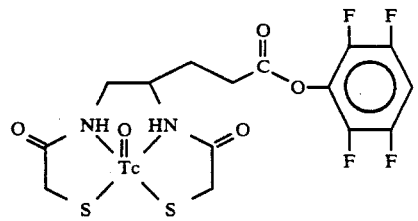

The reaction mixture was constituted by:
1) drying the Tc-99m chelate into a vial
2) adding 1.5 ml t-PA (3 mg)
3) adding 0.45 ml 1M guanidine pH 7
4) adding 1.0 ml 0.5 NaPi pH 10

After 30 minutes at 37° C., the reaction was applied to a suitable gel filtration column such as a column comprising a cross-linked dextran gel, e.g., Sephadex G-25 column equilibrated in an appropriate buffer. The fractions (flow-through) containing the purified, labeled t-PA were collected and characterized by TLC.

Certain variations in this reaction mixture, as well as the preparation of controls and the results achieved, were as follows:

Prep #1

3 mg t-PA
26.7 mCi chelate
pR 10, 37° C., 30 min
reaction TLC 54.5%
Product: 10.7 mCi, 2.67 mCi/mg, TLC=99.4%
Yield: radiochemical (uncorr) 40%, protein 100%
Fibrin binding: 37.9% at 1 mg/ml fibrinogen Prep #2

1.5 mg Fab fragment of an antibody 4.22 mCi chelate
pH 10, 37° C., 10 min
reaction TLC 53.4%
Product: 2.59 mCi, 1.57 mCi/mg, TLC-99.4%
Yield: radiochemical (uncorr) 59.7%, protein 93%

Prep #3

0.9 mg PPACK bound to t-PA
11.8 mCi chelate
pH 10, 37° C., 15 min
reaction TLC not done
Product: 3.25 mCi, 2.81 mCi/mg, TLC=99.2%
Yield: radiochemical (uncorr) 27.5%, protein 66.5%
Fibrin binding: 56.2% at 1.0 mg/ml fibrinogen Prep #4

4.0 mg t-PA
40 mCi chelate
pH 10, 37° C., 30 min
reaction TLC not done
Product: 14.63 mCi, 3.31 mCi/mg, TLC=99.1%
Yield: radiochemical (uncorr) 36.5%, protein 98%
Fibrin binding: 45.0% at 1.0 mg/ml fibrinogen Prep #5

1.2 mg t-PA
17.8 mCi chelate
pH 9, room temperature, 15 min, treat with lysine reaction TLC 50 5%
Product: 3.5 mCi, 2.22 mCi/mg, TLC =98.4%
Yield: radiochemical (uncorr) 19.7%, protein 100%
Fibrin binding: 66.8% at 1.0 mg/ml fibrinogen Prep #6

0.2 mg PPACK bound to t-PA
21.8 mCi chelate
pH 9, room temperature, 25 min, treat with lysine reaction TLC 47%
Product: 1.34 mCi, 6.28 mCi/mg, TLC=98.0%
Yield: radiochemical (uncorr) 6%, protein 93%
Fibrin binding: 65.5% at 1.0 mg/ml fibrinogen Prep #7

1.0 mg PPACK bound to t-PA
41 mCi chelate
pH 9, room temperature, 30 min, treat with lysine reaction TLC not done
Product: 9.96 mCi, 8.15 mCi/mg, TLC=98.7%
Yield: radiochemical (uncorr) 24%, protein 49%
Fibrin binding: 65.2% at 1.0 mg/ml fibrinogen The resulting preparations were administered to rabbits having artificially induced blood clots in the jugular vein The preparations were injected into the ear vein proximal the clot. Unless noted otherwise, all preparations were diluted into a physiologically acceptable solution to a total volume of 8 ml and infused into the rabbit over 10 min.

| Rabbit B, Injection 1 | Prep #3, 2.7 mCi, 0.97 mg PPACK t-PA |
| Rabbit B, Injection 2 | Prep #1, 3.72 mCi, 1.8 mg t-PA |
| Rabbit C, Injection 1 | Prep #4, 4.3 mCi, 1.3 mg t-PA |
| Rabbit C, Injection 2 | Prep #4, 4.0 mCi, 1.3 mg t-PA |
| Rabbit D, Injection 1 | Prep #5, 2.12 mCi, 0.9 mg t-PA |
| Rabbit D, Injection 2 | Prep #6, 0.95 mCi, 0.15 mg PPACK t-PA |
| Rabbit D, Injection 3 | Prep #5, 0.82 mCi, 0.45 mg t-PA, route is opposite ear |
| Rabbit F, Injection 1 | Cold t-PA 1 mg |
| Rabbit F, Injection 2 | Prep #7, 1.61 mCi, 0.26 mg PPACK t-PA |

The rabbits were scanned with a gamma camera at various time points after injection to image the blood clots. FIG. 1 represents four of the resulting scans, taken of rabbit C at the indicated time points after injection #1: immediately after injection and at 5, 10 and 15 minutes after injection. The site of injection is indicated by the thin arrows, and the clot sites are indicated by the heavier arrows. As can be seen, the clot image is darkest at the 5- and 10-minute time points, and had become much fainter only 15 minutes after injection. This animal was injected with preparation #4, in which the $N_2S_2$ chelate was bound directly to the t-PA protein through reaction of the ester group on the chelate with free amine groups on the lysine residues of the protein (i.e., without PPACK linkers). It is believed that the image became faint so quickly due to release of the radiolabeled t-PA from the clot surface during clot dissolution, since the t-PA retains enzymatic activity.

In an effort to prolong the length of time during which imaging can take place, the linker D-Phe-Pro-Arg-CH$_2$Cl (PPACK) was bound to t-PA to inactivate the enzymatic activity thereof. The resulting PPACK-t-PA was reacted with a $^{99m}$TcN$_2$S$_2$ chelate to form a radiolabeled protein conjugate comprising a PPACK linker. This conjugate was injected into rabbits B (injection #1), D (injection #2), and F (injection #2), as indicated above. The scans for D and F showed localized images of the clot for prolonged periods of time (measured in hours rather than minutes), whereas scans for B did not give very good images. While not wishing to be bound by theory, it is believed that administration of active t-PA as injection #1 (unlabeled t-PA for F and $^{99m}$TcN$_2$S$_2$-labeled t-PA for 1)) "opened up" the clot slightly to provide additional binding sites for the $^{99m}$TcN$_2$S$_2$-PPACK-t-PA diagnostic agent, rather than limiting binding of the diagnostic agent to sites only on the outer surface of the clot.

Although prolonged time spans for imaging were achieved by binding PPACK to t-PA to inhibit the enzymatic activity thereof, decreased fibrin binding remained a problem in all preparations. This is believed to be attributable to covalent binding of the $N_2S_2$ chelate to free amine groups in each portion of the protein, including the fibrin-binding portion. Thus, even though PPACK was present on the t-PA in some preparations, binding of the chelate to t-PA was nonspecific, i.e., was not limited to binding through the PPACK linker.

In an effort to achieve specific binding of the radionuclide to the non-fibrin-binding portions of t-PA, while reducing the enzymatic activity thereof, procedures for joining the $N_2S_2$ chelate to the PPACK linker prior to attachment to t-PA were developed. These procedures are described in Example 2.

EXAMPLE 2

Alternative Method for Preparation of
$^{99m}$TcN$_2$S$_2$-D-Phe-Pro-Arg-CH$_2$Cl-t-PA Conjugates An N$_2$S$_2$-D-Phe-Pro-Arg-CH$_2$Cl molecule is chemically synthesized and radiolabeled with $^{99m}$Tc, then conjugated to t-PA, as follows:

Preparation of t-butoxycarbonyl-D-phenylalanine-L-proline-methyl ester (3)

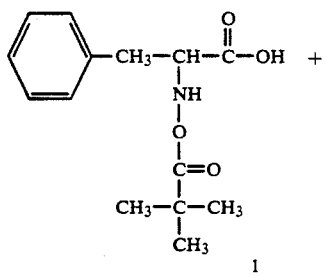
1

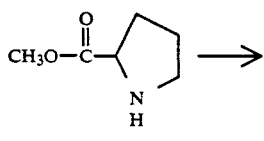
2

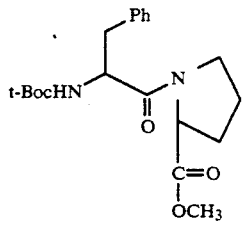
3

One gm (6 mmole) L-proline-methyl ester HCl (Aldrich) was added to 15 ml CH$_2$Cl$_2$. Then 866 1 (1 equiv.) triethylamine (TEA) was added, followed by 1.6 gm (1 equiv.) of T-Boc-D-phenylalanine (Bachem) and 1.6 gm (1.3 equiv.) dicyclohexylcarbodiimide (DCC, Aldrich). The reaction was stirred at room temperature for 3.5 hrs. 1 1,C (CH$_3$CN:H$_2$O:AcOH, 94:5:1, ninhydrin stain) indicated minor amounts of starting materials and a major new product at an R$_f$ of 0.95.

Dicyclohexylurea (DCU) was removed by filtration and washed with CH$_2$Cl$_2$. The organic filtrate was washed with 0.1N HCl, 5% NaHCO$_3$, and H$_2$O, respectively. The CH$_2$Cl$_2$ layer was dried over MgSO$_4$, filtered, and evaporated under reduced pressure, to yield an oil. This oil was applied to a silica gel column (35 cm×2 cm) and eluted with EtOAc:Hex (ethylacetate:-hexane) (4:6). Fractions were monitored by TLC using the same solvent and a KMnO$_4$ stain. Initial fractions (R$_f$0.9) contained a nonpolar impurity. Following fractions contained the desired compound (R$_f$0.4) and were pooled and evaporated to yield 1.54 gm (70%) of a clear, sticky oil.

1H NMR (DCCl$_3$) 7.2 (s, 5H, C$_6$H$_5$), 3.7 (s, 3H, OCH$_3$), 1.9 (m, 4H, (CH$_2$)$_2$), 1.4 (s, 9H, C(CH$_3$)3).

Preparation of D-phenylalanine-L-proline-methyl ester (4)

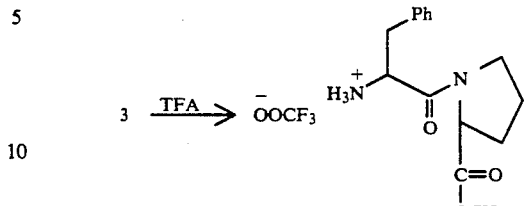
4

To 1.54 gm (4 mmole) of T-Boc-D-Phe-L-Pro-Me (3) 35 ml of trifluoracetic acid was added. This solution was stirred at 0° C. (H$_2$O/ice) for one hr. as the bath gradually rose to room temperature. TLC acetonitrile:-water:acetic acid (EtOAc:Hex, 4:6) using the KMnO$_4$ stain showed complete disappearance of starting material. TLC (CH$_3$CN:H$_2$O:AcOH, 94:5:1, ninhydrin stain) indicated one product (R$_f$0.7).

TFA was removed using reduced pressure. The residue was triturated with diethyl ether and filtered to yield 1.3 gm of a white crystalline solid (81% yield).

$^1$H NMR (DCCl$_3$) 8.2 (br, 1H, NH$_2$), 7.2 (s. 5H, C$_6$H$_5$), 3.5 (s, 3H, OCH$_3$) 1.7 (m, 4H, (CH$_2$)$_2$.

Preparation of succinimidyl-4,5-bis-(S-(1-ethoxy)ethyl mercapto)acetamido pentanoate (5)

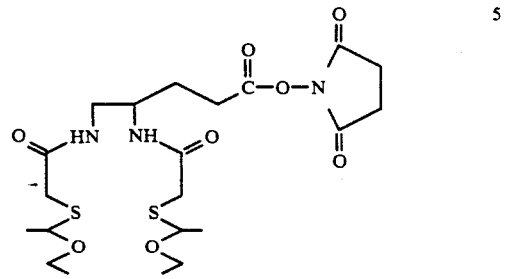
5

Compound 5 is an N$_2$S$_2$ chelating compound comprising (1-ethoxy)ethyl sulfur-protecting groups and a succinimidyl ester group. The synthesis of such chelating compounds, and the radiolabeling thereof with $^{99m}$Tc to form the corresponding chelate, is described in published European patent application publication no. 188,256 and in co-pending patent applications assigned U.S. Ser. Nos. 065,011 and 065,017, both filed Jun. 19, 1987.

One gram (2.36 mmole) of 4,5-bis(s-(S-1-ethoxy) ethyl mercapto)acetamide pentanoic acid [bis-EOE-carboxylic acid] was dissolved in 10.0 ml anhydrous THF. 0.298 (2.59 mmole) of N-hydroxy-succinimide was added, followed by 0.584 9 (2.83 mmole) of dicyclohexylcarbodiimide. The reaction was stirred at room temperature overnight.

TLC (96:4 EtOAc:HOAc p-anisaldehyde stain) analysis indicated absence of bis-EOE-carboxylic acid (R$_f$=0.5) and a new product (Rf=0.65).

Dicyclohexylurea (DCU) was removed by filtration and washed with methylene chloride. The solvents were removed from the filtrate in vacuo to leave an oil. The crude product was purified via flash chromatography (SiO$_2$, 2 cm×45 cm) in 96:4 EtOAc:HOAc. Fractions containing product with an $R_f$ of 0.65 were combined and evaporated. Diethylether trituration and filtration yielded a hygroscopic white solid (0.97 9) in 79% yield.

$^1$H NMR (DCCl$_3$): o 7.25 (m, 2H, NH×2), 4.75 (g, 2H, SCH×2) 3.3 (S, 4H, SCH$_2$×2), 2.85 (S, 4H, NHS (CH$_2$)$_2$), 1.55 (d, 6H, CH$_3$CH×2), 1.2 (t, 6H, CH$_3$CH$_2$×2).

Preparation of 4,5-bis-(S-1-ethoxy)ethylmercapto)acetamidopentanoyl-D-phenylalaninyl-L-prolyl methyl ester (6)

4 + 5 ⟶

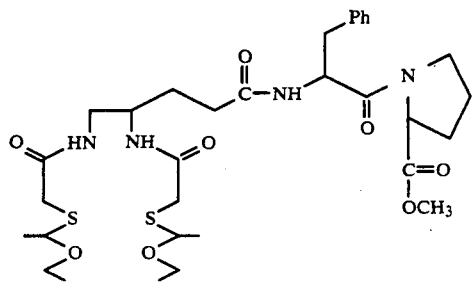

6

To 849 mg (2.18 mmole) of D-He-Pro-Me(4), 5 ml of anhydrous DMF was added. 314 1 triethylamine (1 equiv.) was added, followed by 1.13 (1 equiv.) of bis-ethoxy-carboxylic acid NHS ester (5). The reaction was stirred overnight.

TLC (EtOAc:AcOH, 96:4 p-anisaldehyde) indicated the disappearance of the NHS ester ($R_f$ 0.9) and the appearance of a new product ($R_f$ 0.8). DMF was removed under reduced pressure and the residue taken up in ELOAc. The EtOAc was washed with 0.1N HCl 5% NaHCO$_3$, and twice with H$_2$O. The organic layer was aired over MgSO$_4$, filtered, and evaporated to yield 1.1 gm (63%) of an oil.

This oil was purified by flash chromatography using a silica gel column (45 cm×2 cm). The desired compound was eluted using EtOAc:AcOH (96:4, p-anisaldehyde stain). Fractions containing product were combined to yield 600 mg (35%) of a clear oil.

$^1$N NMR (DCCl$_3$) 300 MH$_2$ ō 7.15 (m, 5H, C$_6$H$_5$) (s, 3H, OCH$_3$) 1.5 (m, 6H, CH$_3$CH×2) 1.18 (m, 6H, CH$_3$CH$_2$).

Preparation of 4,5-bis-(S-(1-ethoxy)ethylmercapto) acetamidopentanoyl-D-phenylalaninyl-L-proline (7)

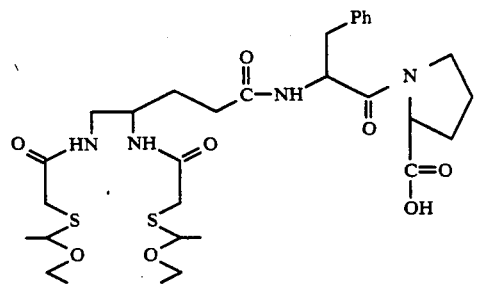

7

To 600 mg (0.75 mmole) of bis-ethoxy-Phe-Pro-Me (6), 5 ml MeOH was added. 0.75 ml (1 equiv.) of 1N NaOH was added and the solution became cloudy. After 1 hr, a new product appeared at an $R_f$ of 0.2 by TLC (CH$_3$CN:H$_2$O: AcOH, 94:5:1) with a large amount of starting material. The reaction was run overnight. TLC indicated same starting material still present. 350 1 (0.5 equiv.) additional 1N NaOH was added. After 2 hrs, the new product was considered the major spot by TLC.

Solvents were removed to leave a white residue. This residue was taken up in EtOAc and washed twice with 1M AcOH and twice with H$_2$O. The organic layer was then dried over MgSO$_4$, filtered, and (82%) evaporated to leave 484 mg of a sticky white solid.

The compound was purified by flash chromatography using silica gel (25 cm×1.5 cm) and CH$_3$CN:H$_2$O:-HOAc as an eluting solvent. Once the desired compound began coming off the column, the solvent ratio was changed to 92:6:2 and elution was continued until no more compound was evident in the eluent by TLC. All solvents were removed and the final product dried under high vacuum. Yield: 460 mg (78%).

$^1$N NMR (DCCl$_3$) 60 MHz ō 7.2 (s, 5H, C$_6$H$_5$) 3.3 (s, 4H, SCH$_2$×2), 1.6 (d, 6H, CH$_3$CH), 1.2 (t, 6HG, CH$_3$CH$_2$).

Preparation of 4,5-bis-(S-1-ethoxy)ethylmercapto) acetamidopentanoyl-D-phenylalaninyl-prolyl-D-Y-N-nitro arginine chloromethyl ketone (9)

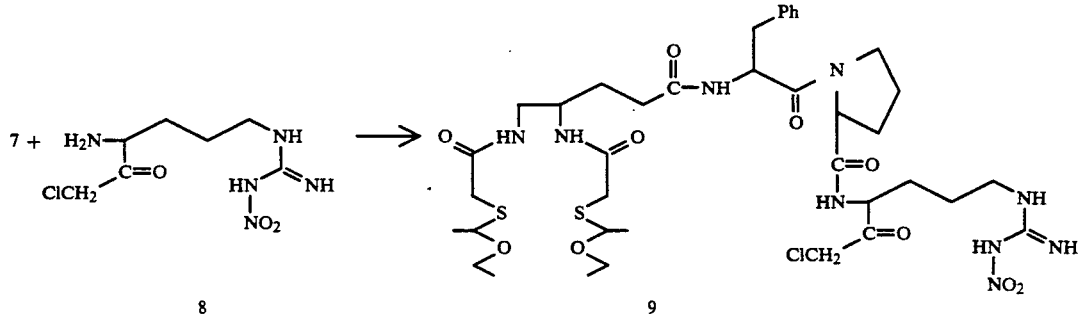

Bis-ethoxy-Phe-Pro (7) (0.1 g. 0.26 mmole) is reacted with N-methylmorpholine (0.028 ml, 0.26 mmole) in 1.2 ml of THF for 10 min at −20° C. Cold THF (5 ml) containing isobutylchloroformate (0.035 ml, 0.26 mmole) is added to the mixed anhydride preparation, and the mixture is immediately added to H-Arg(NO₂)CH₂Cl HCl (8) (0.073 g, 0.26 mmole) dissolved in 1.2 ml of cold DMF (Kettner and Shaw, *Biochem.* 17(22): 4780 (1978). The reaction is stirred for 1 hr at −20° C. and 2 hrs at room temperature, then filtered. The filtrate is evaporated to dryness, and the residue is dissolved in 1 ml of methanol. The solution is diluted to 24 ml with ethyl acetate and then washed with 0.1N HCl, 5% NaHCO3, and saturated aqueous NaCl. The organic phase is dried over anhydrous Na₂SO4 and concentrated in vacuo to yield (9).

Preparation of 4,5-bis-(S-1-ethoxy)ethylmercapto) acetamido pentanoyl-D-phenylalaninyl-L-Prolyl-D-arginine chloromethyl ketone (10)

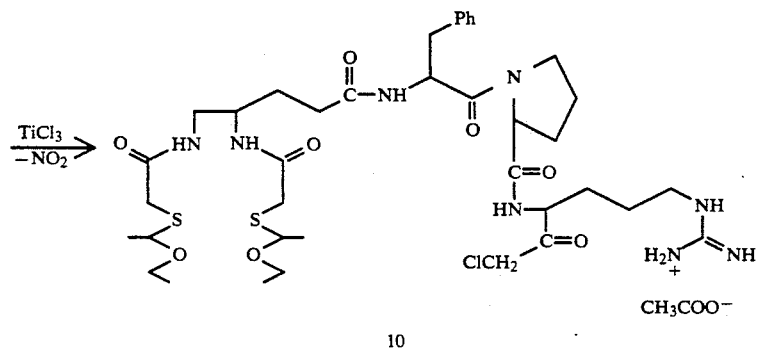

10

The nitro-arginine derivative (9) is taken up in MeOH and treated under N₂ with a freshly prepared buffered solution of TiCl₃ made from 20% aqueous TiCl₃ and 4M aqueous ammonium acetate, as described in Freidinger et al., *J. Org. Chem.* 43: 4800 (1978). Due to the propensity for chloromethyl ketone groups to reduce in the presence of TiCl₃, as described by Clerici et al., *Tet. Lett.* 28: 1547 (1987), the pH of the ammonium acetate may be lowered, using AcOH, to maximize reduction of the nitro group and minimize chloromethyl ketone reduction.

The resulting N₂S₂-D-Phe-Pro-Arg(CH₂Cl) molecule (i.e., compound 10) is radiolabeled with $^{99m}$Tc as follow, to form a compound of the following formula, comprising the corresponding $^{99m}$TcN₂S₂ chelate:

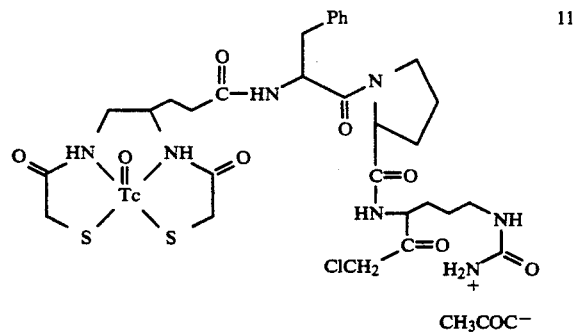

One ml of sterile water for injection is added to a sterile vial containing a stannous gluconate complex (50 mg sodium gluconate and 1.2 mg stannous chloride dihydrate, available from Merck Frosst, Canada, in dry solid form), and the vial is gently agitated until the contents are dissolved. A sterile insulin syringe is used to inject 0.1 ml of the resulting stannous gluconate solution into an empty sterile vial. Sodium pertechnetate (0.75 ml, 75.100 mCi, eluted from a $^{99}$Mo/$^{99}$Tc generator purchased from DuPont, Mediphysics, Mallinckrodt, or E. R. Squibb) is added, and the vial is agitated gently to mix the contents, then incubated at room temperature for 10 min to form a $^{99m}$Tc-gluconate complex. This complex is an intermediate or "exchange complex" in which the $^{99m}$Tc radionuclide is bound temporarily until it is exchanged into the N₂S₂ chelating compound.

0.87 ml of 100% isopropyl alcohol is added to a vial containing compound 10, prepared above, in dry solid form. The vial is shaken gently to dissolve the compound. Next, 0.58 ml of this solution is transferred to a vial containing 0.16 ml of glacial acetic acid/0.2N HCl (2:14), and the vial is gently agitated. Of this acidified solution, 0.5 ml is transferred to the vial containing the $^{99m}$Tc-gluconate complex, prepared above. After gentle agitation to mix, the vial is incubated in a 75° C.±2° C. water bath for 15 min, then immediately transferred to a 0° C. ice bath for 2 min to stop the reaction, thereby forming (11).

The $^{99m}$TcN₂S₂-D-Phe-Pro-Arg-CH₂Cl compound (11) was combined with t-PA in a buffered solution to produce the radiolabeled t-PA complex as follows:

5 ml H₂O was added to a 50 ng vial of Activase and allowed to stand at room temperature for 20 min. The protein solution was then exchanged into a buffer containing 0.2M arginine, 0.01M Na Phosphate pH 7.2 using a gel filtration column. To the $^{99}$Tc-N₂S₂-labeling mixture was added 1.0M tris base to bring the pH of the mixture to 7.7. The labeling mixture and the t-PA solution were then combined in 1:1 molar ratio, and incubated at 37° C. for 10 minutes. (The pH of this final mixture should be no lower than 7.2, and no higher than 8.2.) Residual t-PA activity was eliminated by adding a several-fold molar excess of PPACK. The protein was then desalted on a gel filtration column which also removes unincorporated 99Tc, PPACK, and 99Tc-N₂S₂ PPACK. This column was equilibrated with 0.2M Arginine, 10 mM Na Phosphate pH 7.2. The protein containing fraction was then used for imaging studies.

Figure 6:
FIG. 6 shows the image of a jugular vein fibrin-platelet clot using a labeled thrombolytic protein.

When compound 11 was administered over a 20 minute infusion through the marginal ear vein of a rabbit in which a preformed thrombus resided in the jugular vein, the thrombus was imaged during the infusion. The image was still apparent 60 minutes after the end of the infusion (FIG. 6).

EXAMPLE 3

Figure 2:
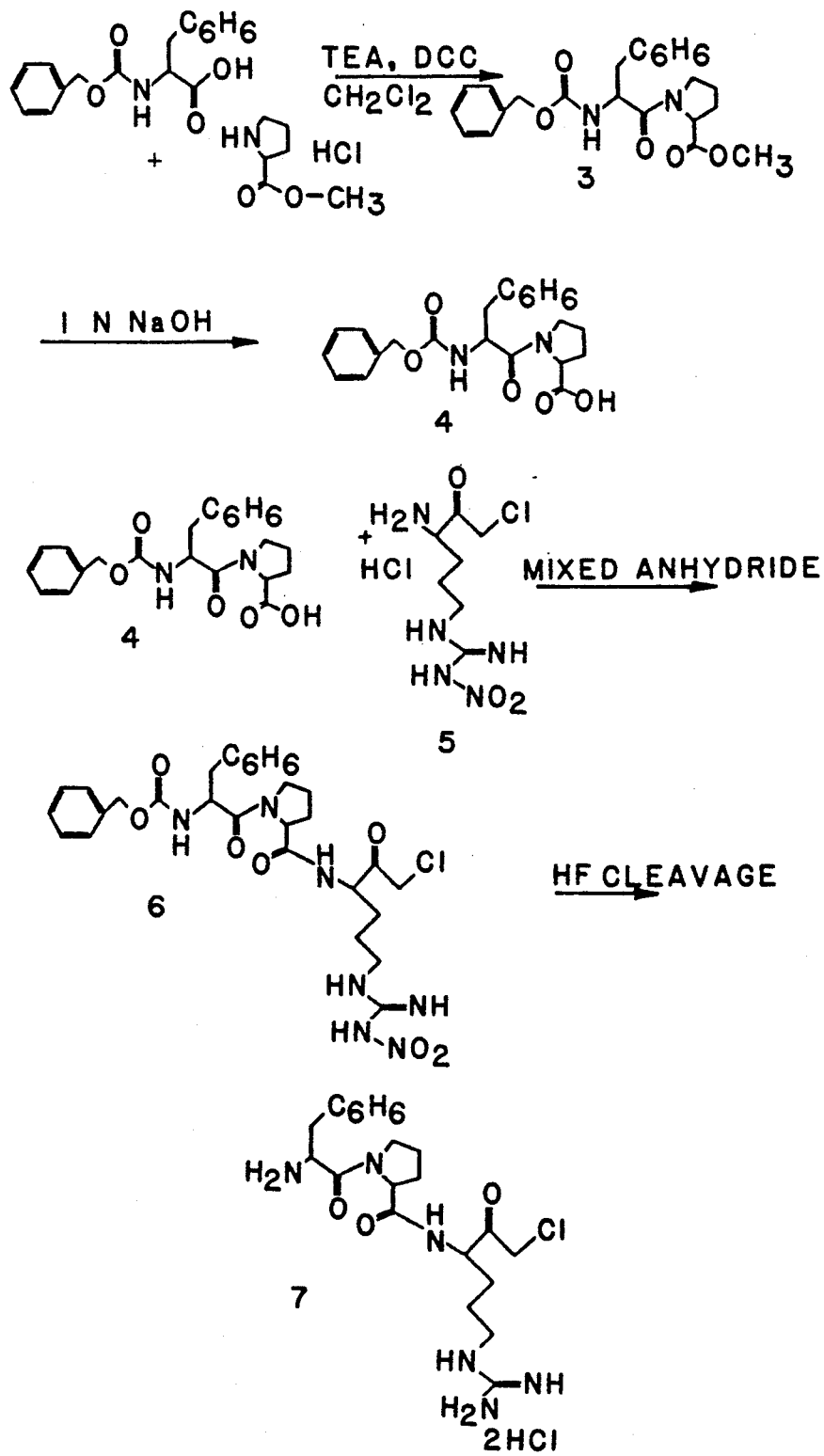
FIG. 2 depicts a scheme for synthesizing a D-Phenylalanine-Proline-Arginine-CH$_2$Cl linker.

Synthesis of a D-Phe-Pro-Arg-CH$_2$Cl Linder and Attachment Thereof to an N$_2$S$_2$ Chelating Compound This synthetic scheme is depicted generally in FIG. 2. The linker is synthesized using a variation of the procedures described by Kettner and Shaw (*Biochemistry.* 17 [1978]p. 4780) for the synthesis of tripeptide derivatives.

Synthesis of Compound 3

Cbz-D-Phe and Pro-Me are added to CH$_2$Cl$_2$. 1 equiv. of dicyclohexyl carbodiimide (DCC) and triethyl amine (TEA) are added and the reaction is stirred overnight. TLC in EtOAc: Hexane (1:1), visualized by KMnO$_4$ shows product at an R$_f$ of 0.6. Dicyclohexylurea (DCU) is filtered off and the organic layer is washed with 0.1N HCl, 5% NaHCO$_3$, and brine, respectively. The CH$_2$Cl$_2$ is dried over MgSO$_4$, filtered, and evaporated to yield Compound 3. Excess DCU can be removed by filtration from cold CH$_3$CN.

Synthesis of Compound 4

Compound 3 is stirred in methanol containing 1.4 equiv. of 1N NaOH overnight. The product can be seen on TLC (EtOAc: AcOH 96:4) at an R$_f$ of 0.5 by visualization with PAA. After the reaction is complete solvents are removed and the residue is taken up in EtOAc. The solution is washed with 0.1N HCl and H$_2$O. The organic layer is dried over MgSO$_4$, filtered, and evaporated. The product was purified on a silica gel column using 100% CH$_3$CN.

Synthesis of Compounds 5, 6, and 7

Compounds 5, 6, and 7 were synthesized as described in the publication by Kettner and Shaw supra (which is hereby incorporated by reference) and as shown in FIG. 2. The mixed anhydride product (6) was purified on a silica gel column using 100% EtOAc. Compound 7, which is D-Phe-Pro-Arg-CH$_2$Cl (i.e., PPACK) is then attached to a chelating compound.

Synthesis of Compound 8

Figure 3:
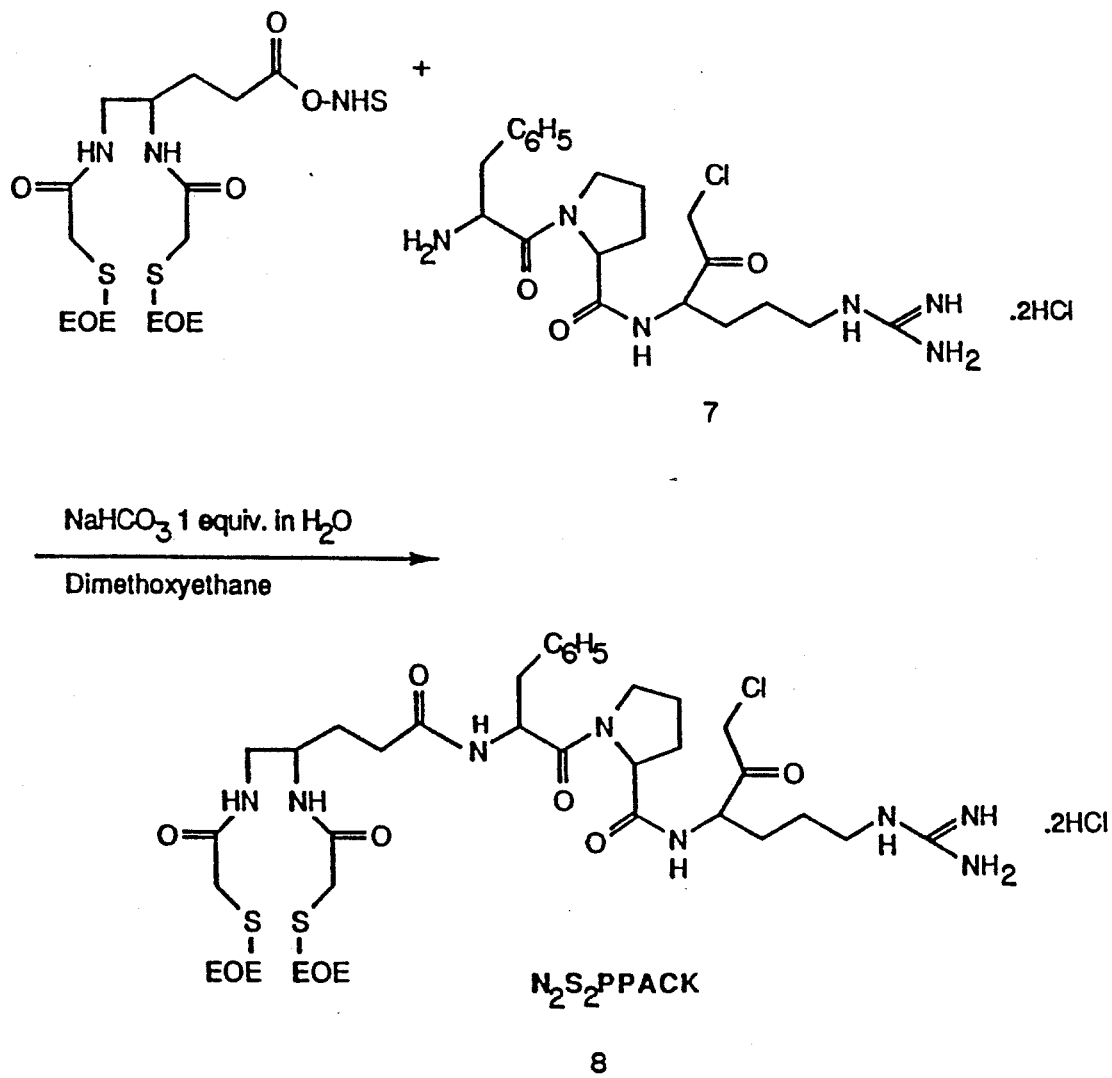
FIG. 3 depicts the reaction of a chelating compound with a D-Phenylalanine-Proline-Arginine-CH$_2$Cl linker.

As depicted in FIG. 3, the PPACK linker is attached to an "N$_2$S$_2$" chelating compound comprising ethoxyethyl (EOE) sulfur protecting groups and an N-hydroxy succinimidyl ester. The ester reacts with a primary amine group on the linker to join the chelating compound thereto. The reaction is as follows:

PPACK is taken up in H$_2$O and 1 equiv. of NaHCO$_3$. The pH is prior to the addition of NaHCO$_3$ and 6 after the addition. This pH is specific for reaction at the Phe amino group over the guanidium group of arginine. One equivalent of the chelating compound is taken up in dimethoxyethane (DME) and added to the aqueous solution over a period of 30 minutes. TLC in nBuOH: AcOH: H$_2$O (4:1:1) indicates a new spot at an R$_f$ of 0.5, between the two starting materials, that stains in both para-anisaldehyde and ninhydrin. After 2 hours the solvents are removed. The compound 8 is purified directly on a silica gel column using deactivated silica gel and eluted with CH$_2$Cl$_2$: MeOH: AcOH (85:13:2).

Radiolabeling and Binding to t-PA

Compound 8 is radiolabeled to produce a $^{99m}$Tc-N$_2$S$_2$ radionuclide metal chelate joined to the PPACK linker. The radiolabeling procedure is as described in Example 2 above. The resulting $^{99m}$Tc-N$_2$S$_2$-D-Phe-Pro-Arg-CH$_2$Cl compound is combined with t-PA in a buffered solution, whereupon the radionuclide metal chelate is attached to t-PA through the linker.

Alternative Linker

The amino acid tyrosine may be substituted for phenylalanine in the above procedure to produce the linker Tyr-Pro-Arg-CH$_2$Cl. A radionuclide metal chelate may be attached to t-PA through this linker as described above for the N$_2$S$_2$ chelate and the D-Phe-Pro-Arg-CH$_2$Cl linker.

EXAMPLE 4

Figure 4:
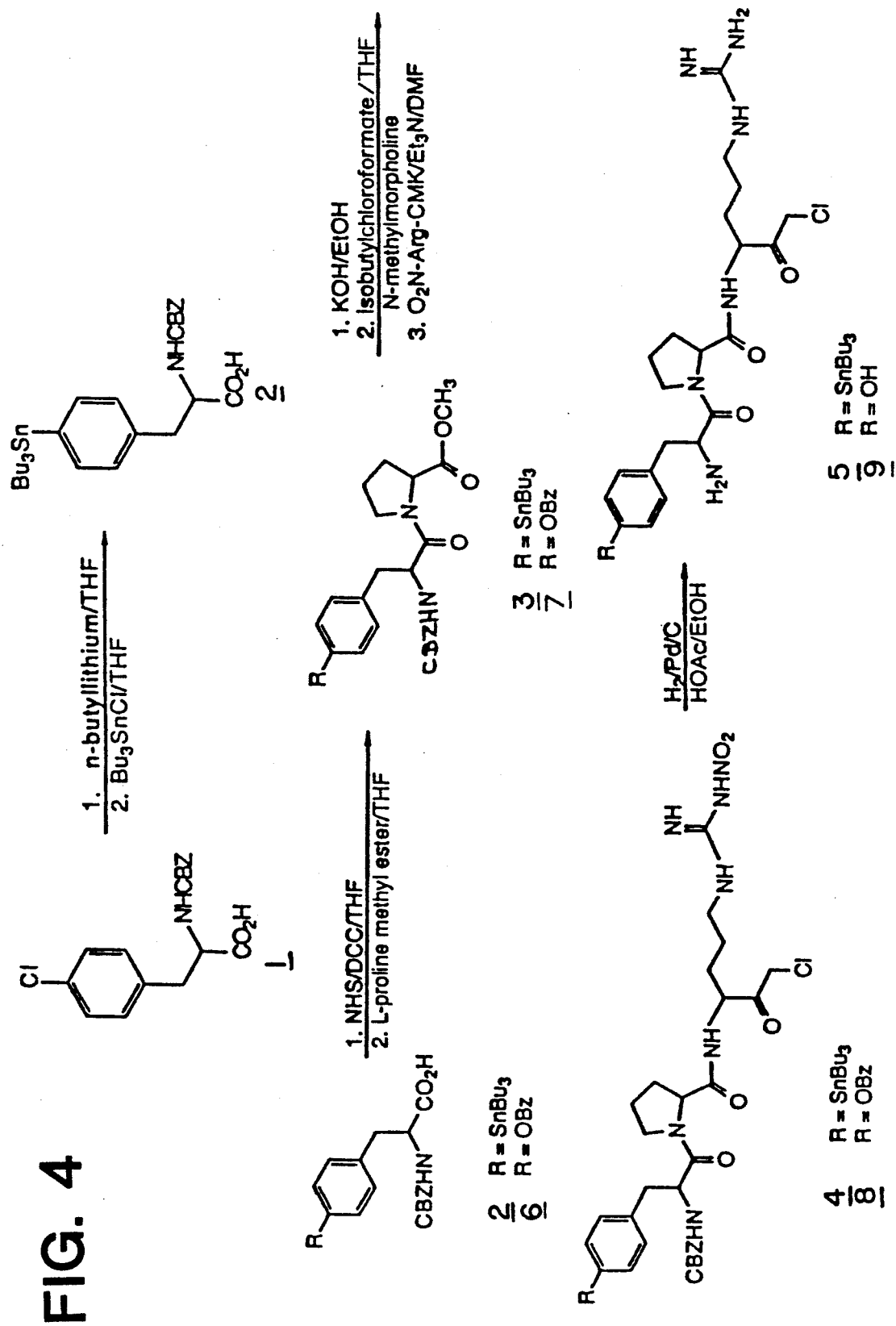
FIG. 4 depicts the synthesis of two different tripeptide. chloromethyl ketone derivatives which are useful as linkers.
Figure 5:
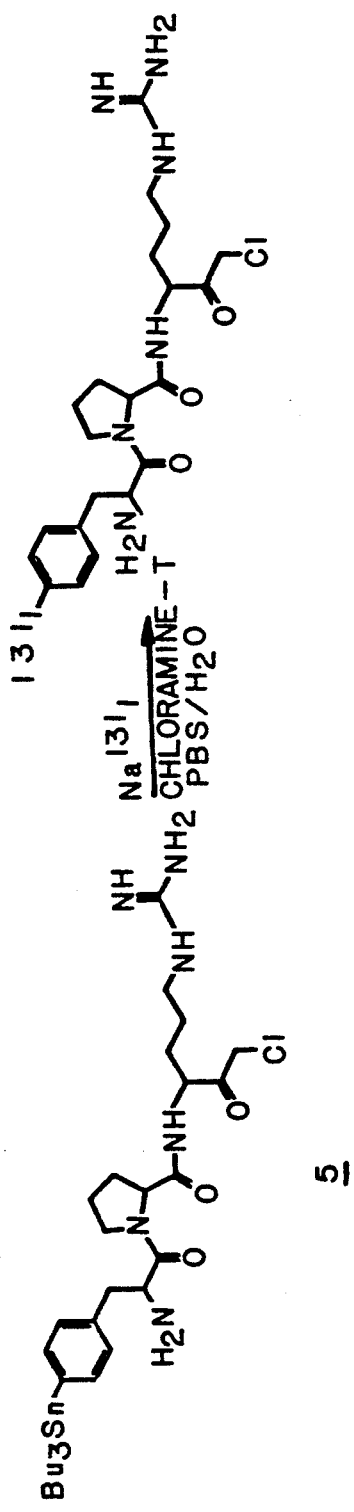
FIG. 5 shows two radioiodinated linkers that may be bound to t-PA.
Figure 5:
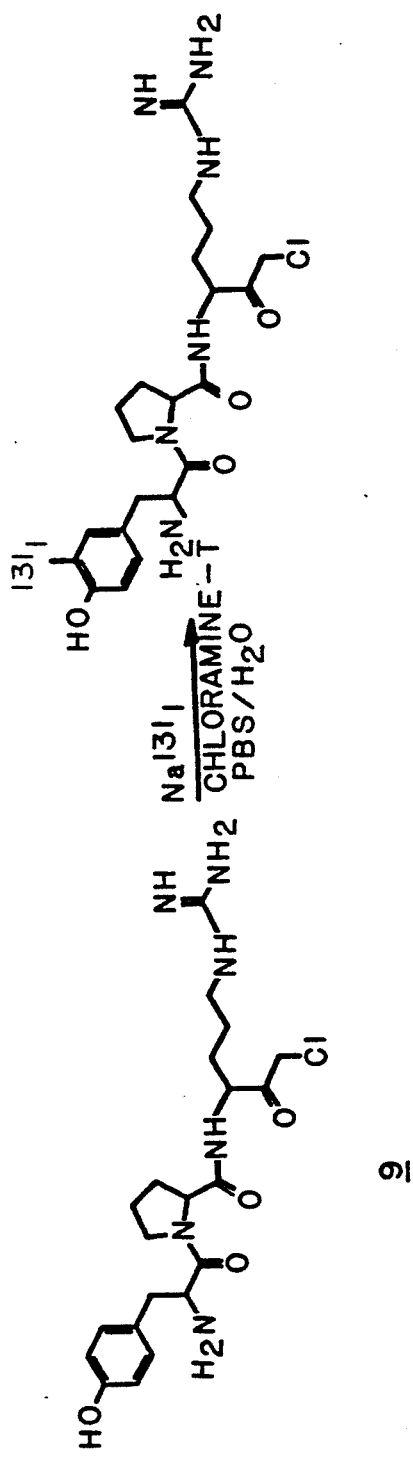

Production of Radioiodinated D-Phe-Pro-Arg-CH$_2$Cl Linker and Binding Thereof to t-PA The synthesis procedure is generally depicted in FIGS. 4 and 5.

Synthesis of N-CBZ p-tri-n-butylstannyl phenylalanine (2)

To a solution of N-CBZ p-chloro phenylalanine 1 (one equivalent) in anhydrous THF at 100° C. is added n-butyllithium (3.3 equiv.). After one hour, a solution of Bu$_3$SnCl (excess) is added. Other tri-alkyl-Sn compounds may be used in place of Bu$_3$SnCl. The solution is warmed to 0° C. and quenched by the addition of saturated NH$_4$Cl. Extractive work-up into diethyl ether affords the desired product.

Synthesis of N-CBZ p-tri-n-butylstannyl Phe-Pro-methylester (3)

To a solution of N-CBZ p-tri-D-Butylstannyl Phe (2) (1 equiv.) in anhydrous THF at 0° C. is added dicyclohexyl carbodiimide (1.2 equiv.) followed by N-hydroxysuccinimide (1.2 equiv.). The resulting solution is stirred overnight. The mixture is filtered, the filtrate concentrated, and the crude residue is chromatographed. To a solution of the purified NHS ester in THF is added a THF solution of proline methyl ester. The resulting solution is stirred overnight. The mixture is filtered, the filtrate concentrated and the crude residue is chromatographed to afford N-CBZ p-tri-D-Butylstannyl Phe-Pro-methylester. (3)

Synthesis of N-CBZ p-tri-n-butylstannyl Phe-Pro-NO$_2$ Arg (CMK) (4)

To a solution of N-CBZ p-tri-D-Butylstannyl Phe-Pro-methylester (3) in 95% ethanol is added KOH (5–10 equiv.). The resulting solution is warmed slightly for several hours. The solution is cooled to 0° C. and acidified with cold aqueous HCl. Extractive work-up affords the desired carboxylic acid. To a solution of the carboxylic acid in THF is added isobutyl chloroformate (1 equiv.) in the presence of N-methylmorpholine (1 equiv.) and the mixture is reacted for an hour at −20° C. Cold triethylamine (1 equiv.) is added and the resulting mixture is immediately added to a solution of nitroarginine chloromethyl, ketone-HCl (1 equiv.) in cold DMF. After stirring for 1 hour at 20° C. and 2 hours at room temperature, the reaction mixture is filtered and concentrated to dryness. Extractive work-up into ethyl acetate affords the desired product. (4)

Synthesis of p-tri-n-butylstannyl Phe-Pro-Arg (CMK) (5)

To a solution of N-CBZ-p-tri-D-Butylstannyl Phe-Pro-NO$_2$ Arg (CMK) (4) in acetic acid/ethanol solution was added palladium on activated charcoal. The resulting mixture was hydrogenated for several days at 30 psi. The catalyst is removed by filtration through Celite. The filtrate is diluted with water and washed with ether. The aqueous phase is then lyophilized to afford the product (5).

Radioiodination of p-tri-n-butylstannyl Phe-Pro-Arg (CMK) (5)

To a vial containing Na$^{131}$I solution in 0.1N NaOH (up to 10 mCi) is added p-tri-D-Butylstannyl Phe-Pro-Arg (CMK) (5) (50 g. $7.1 \times 10^{-2}$ μmol) in PBS (phosphate buffered saline). To this solution is added a solution of chloramine-T in water (160 μg, 0.71 μmol in 160 μl water). After 3.5 minutes, Na$_2$S$_2$O$_5$ is added (70 μl of a 1.0 mg/ml solution of Na$_2$S$_2$O$_5$ in water). The resulting radioiodinated PPACK linker is depicted in FIG. 5. The $^{131}$I radionuclide is substituted directly onto the aromatic ring of the phenylalanine residue of the linker.

The radioiodinated compound is combined with t-PA in a buffered solution, whereupon it binds to the t-PA.

EXAMPLE 5

Production of Radioiodinated Tyr-Pro-Arg-CH$_2$Cl Linker and Binding Thereof to t-PA The synthesis procedure is generally depicted in FIGS. 4 and 5.

Synthesis of Tyr-Pro-Arg (CMK) (9)

The synthesis of Tyr-Pro-Arg- (CMK) (9) is accomplished as described for p-tri-D-Butylstannyl Phe-Pro-Arg (CMK) (5) by replacement of N-CBZ-p-tri-D-Butylstannyl Phe (2) with O-benzyl-N-CBZ tyrosine (6). This O-benzyl-N-CBZ tyrosine (6) is coupled to proline methyl ester, the resulting dipeptide is hydrolyzed to the acid and then coupled to NO$_2$ arginine CMK. Hydrogenation removes the NO$_2$, benzyl, and CBZ protecting groups to afford the desired compound (9).

Radioiodination of Tyr-Pro-Arg (CMK) (9)

Radioiodination of Tyr-Pro-Arg- (CMK) (9) is accomplished as described for p-tri-D-Butylstannyl Phe-Pro-Arg (CMK) (5). The resulting radioiodinated compound (shown in FIG. 5) is reacted with t-PA in a buffered solution, whereupon the compound binds to t-PA.

What is claimed is:

1. A method for detecting a fibrin-platelet clot in vivo, comprising the steps of:

(a) intravenously administering to a patient suspected of having a fibrin-platelet clot a radiolabeled thrombolytic protein wherein the radiolabeled thrombolytic protein's clot-dissolving activity is eliminated or reduced to a degree sufficient to prolong localization of the protein at a fibrin-platelet clot, compared to localization of a corresponding native protein at a fibrin-platelet clot, and the radiolabel is selectively attached through a linker that binds specifically to a portion of the thrombolytic protein other than a fibrin-binding domain; and (b) detecting the biodistribution of the radiolabeled thrombolytic protein in the patient.

2. The method of claim 1 wherein said radiolabeled thrombolytic protein is t-PA.

3. The method of claim 1 or 2 wherein said radiolabel is a radionuclide metal bound within a chelate.

4. The method of claim 3 wherein said radionuclide metal is $^{99m}$Tc and detecting the biodistribution of the $^{99m}$Tc is by scanning the patient with a gamma camera.

5. The method of claim 1 wherein said radiolabeled substance is attached to the thrombolytic protein through a linker which specifically binds to a clot-dissolving portion of the thrombolytic protein.

6. The method of claim 5 wherein said thrombolytic protein is a fibrin-binding serine protease and the linker is an oligopeptide chloromethyl ketone that binds to the clot-dissolving portion of the serine protease.

7. The method of claim 6 wherein said thrombolytic protein is t-PA and said linker is selected from D-Phe-L-Pro-L-Arg-CH$_2$Cl or Tyr-L-Pro-L-Arg-CH$_2$Cl.

8. The method of claim 5, 6, or 7 wherein said radiolabel is a radionuclide metal bound within a chelate.

9. The method of claim 1 wherein said clot-dissolving activity is essentially eliminated.

10. A thrombolytic protein having a radioisotope attached thereto, wherein the radioisotope is attached to said thrombolytic protein through a linker that binds specifically to a portion of the protein other than a fibrin-binding domain.

11. The thrombolytic protein of claim 10, wherein the thrombolytic protein is t-PA and the linker is derived from an oligopeptide chloromethyl ketone inhibitor of t-PA.

* * * * *

UNITED STATES PATENT AND TRADEMARK OFFICE
CERTIFICATE OF CORRECTION

PATENT NO. : 5,217,705
DATED : June 8, 1993
INVENTOR(S) : John M. Reno, et al.

It is certified that error appears in the above-indentified patent and that said Letters Patent is hereby corrected as shown below:

On the title page, item:

[73] (Assignee) "NeoRx Corporation, Seattle, Washington," should be —NeoRx Corporation, Seattle, Washington, and Genentech, Inc., South San Francisco, California—

Signed and Sealed this

Seventh Day of November, 1995

Attest:

BRUCE LEHMAN

Attesting Officer      Commissioner of Patents and Trademarks